US007000873B2

(12) United States Patent
Metelski (10) Patent No.: US 7,000,873 B2
(45) Date of Patent: Feb. 21, 2006

(54) MICROSCOPE STAND HAVING BALANCING DEVICE

(75) Inventor: Andrzej Metelski, Romanshorn (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 468 days.

(21) Appl. No.: 10/010,101

(22) Filed: Nov. 8, 2001

(65) Prior Publication Data

US 2002/0121577 A1 Sep. 5, 2002

(30) Foreign Application Priority Data

Nov. 12, 2000 (DE) ................................ 200 19 105

(51) Int. Cl.
A47F 5/00 (2006.01)
(52) U.S. Cl. .............. 248/123.11; 248/648; 248/162.1; 248/364; 73/862.392; 73/862.393; 254/390
(58) Field of Classification Search ........... 248/123.71, 248/648, 162.1, 182.1, 364, 123.2, 124.1, 248/125.2, 280.11, 292.11, 284.1, 297.11, 248/572, 571, 331, 332, 334.1; 73/862.392, 73/862.393, 862.49, 829, 856; 254/390, 254/393, 394, 397
See application file for complete search history.

(56) References Cited

U.S. PATENT DOCUMENTS

| 3,889,728 | A | * | 6/1975 | Riche | ........................ | 141/387 |
| 4,252,162 | A | * | 2/1981 | Le Devehat | ................. | 141/387 |
| 4,544,121 | A | * | 10/1985 | Komura | ....................... | 248/331 |
| 4,685,648 | A | * | 8/1987 | Dobner et al. | .............. | 248/572 |
| 4,738,448 | A | * | 4/1988 | Liester | ........................ | 473/483 |
| 5,253,832 | A | | 10/1993 | Bolas et al. | | |
| 5,397,323 | A | | 3/1995 | Taylor et al. | | |
| 5,746,404 | A | * | 5/1998 | Merko | .................... | 248/123.11 |
| 5,984,811 | A | * | 11/1999 | Taylor | ......................... | 473/483 |
| 6,070,839 | A | | 6/2000 | Brenner et al. | | |
| 6,105,909 | A | * | 8/2000 | Wirth et al. | .............. | 248/123.2 |

FOREIGN PATENT DOCUMENTS

| DE | 221 571 A1 | 4/1985 |
| DE | 3739080 A1 | 11/1989 |
| DE | 197 42 050 A1 | 3/1999 |
| DE | 10142564 A1 * | 4/2002 |
| EP | 0 433 426 B1 | 2/1994 |
| EP | 0 700 665 A1 | 3/1996 |
| WO | WO 97/13997 | 10/1995 |
| WO | WO 99/01693 | 6/1997 |

* cited by examiner

Primary Examiner—Kimberly Wood
(74) Attorney, Agent, or Firm—Hodgson Russ LLP (57) ABSTRACT

The invention relates to a stand having a pivotable support arm (2) and a balance weight (AG), in which the balance weight (AG) acts via a cable pull (24) for the weight compensation of the load (G), the balance weight (AG) being arranged in the area of the vertical upright column (21) of the stand.

35 Claims, 9 Drawing Sheets

MICROSCOPE STAND HAVING BALANCING DEVICE

CROSS REFERENCE TO RELATED APPLICATIONS

This invention claims priority of the German application 200 19 105.5 filed Nov. 12, 2000 which is incorporated by reference herein.

The complete disclosures of the following three copending, commonly-owned U.S. patent applications filed concurrently with the present application are hereby incorporated by reference into the present specification: U.S. patent application Ser. No. 10/010,103 filed Nov. 8, 2001, now U.S. Pat. No. 6,708,936; U.S. patent application Ser. No. 10/008,285 filed Nov. 8, 2001, now U.S. Pat. No. 6,637,274; and U.S. patent application Ser. No. 10/007,168 filed Nov. 8. 2001, now U.S. Pat. No. 6,691,960.

FIELD OF THE INVENTION

The invention relates to a stand, in particular for surgical microscopes. Surgical microscopes must be capable of pivoting easily over a predefined range and they should maintain the position then set. For this reason, in a group of known stands, balance weights are provided which compensate for the weight of the microscope and its additional devices. The balance weights are most frequently arranged in the manner of beam-type balances. Particular embodiments of such beam-type balance arrangements are, for example, the "OHS™" design of the applicant, in which balance weights are displaced from top to bottom via parallelogram carriers so that the overall center of gravity of the stand is situated in the lower region of the stand structure. The basic design of the OHS™ is illustrated symbolically in the international Patent Application WO 97/13997 (1997).

BACKGROUND OF THE INVENTION

The weight compensation for the easy operability of a microscope or the mobility of the same in space and for the compensation in this regard of changes in weight at the microscope as a result of adding or removing additional devices to or from the microscope is carried out, in the case of a known stand "MS 1" from the applicant, via a compression spring, which supports a parallelogram carrier diagonally. In the case of the MS 1 design, this parallelogram carrier serves as a pivotable horizontal carrier for the microscope. The particular parallelogram construction has been disclosed by the applicant in the European Patent Application EP 433426 A1 (WO 91/472). The design of the MS 1 is illustrated symbolically in the international Patent Application WO 99/1693 (1999).

For the purpose of improved tilting behavior of the stand, the MS 1 provides a switch box as a balance weight, the box containing both the electrical power supply for the microscope and its lighting device, its control systems and the like and, if appropriate, an additional weight. The switch box is mounted rigidly on the vertical upright column of the stand and there performs only balancing around the vertical axis of the vertical upright column with regard to improving the tilting moment of the stand.

DE 19742050 A1 (1999) makes reference to an article "Gewichtsausgleich an feinmechanischen Geräten" [Balancing on precision mechanical devices] by H. Hilpert in Issue February 1965 of the Journal Feingerätetechnik [Precision Engineering], Volume 14.

In this article, from the year 1965, various weight-compensating measures in precision engineering are discussed, being achieved primarily not by counterweights but by means of spring-compensating measures (such as, by way of comparison, also in the case of the parallel support construction of the MS 1).

DD 221571 A1 (1985) shows a stand design having a lever arm which is weight-compensated by a spring that is connected to the lever arm via a cable pull. The surgical microscope is located at the distal end of the lever arm. The basic adjustment of this surgical microscope is performed via a threaded spindle, with which the end of the spring fixed to the frame is drawn further away from the lever arm or guided closer to it. Changes in weight at the microscope are compensated for by the fact that the pivoting point of the cable pull relative to the lever arm is adjusted via a spindle.

In order to achieve a uniform countermoment in all the possible angular positions of the stand, it is necessary for the aforementioned point of action of the cable pull to be located on a connecting line between the axis of rotation of the lever arm and the mass center of gravity of the microscope. This is achieved by operating an adjusting device in the form of a worm, which rotates a disc connected to the lever arm about the axis of rotation of the lever arm.

In this design, a range of adjustment measures are therefore necessary in order to achieve the desired effect. Apart from this, the construction of this known design necessitates a high overall center of gravity of the stand, since all the balancing devices are arranged above the microscope.

DE 3739080 A1 (1989) likewise specifies a spring device for balancing for stands in which cable pulls in combination with springs are intended to lead to balancing. However, this concerns the provision of force support for an adjusting movement which is exerted by an operator on a handle. However, it does not concern holding a load in a "floating state", as is desired in the case of surgical microscopes.

By contrast, U.S. Pat. No. 5,397,323 (1992) presents a surgical robot having parallelogram carriers, in which, inter alia, the weight of the instrument is held in a weight-compensated fashion via a cable pull with the aid of a counterweight. In this case, the cable pull is of closed design, that is to say one cable in each case is guided from the instrument up to the counterweight over an upper and lower deflecting roller (FIG. 3 of US -323).

Such a design presupposes that the counterweight is fitted in the immediate vicinity of the instrument. It could therefore be applied only poorly for use on a surgical microscope.

DE 19742050 A1 (1999) discloses a stand design having a pivotable parallelogram carrier which is weight-compensated via a cable pull and a balancing spring such that the balancing weights are additionally present and which act in accordance with the balance principle mentioned above can be designed to be particularly small. In the case of this design, the cable pull is guided in a special way in order to minimize the balancing error caused by the finite deflecting radius over a wide pivoting range of the pivoting arm. The balancing error is, however, not eliminated by this measure, and so in specific pivoting positions, adjustment of the balancing weights is still required in order to achieve the desired balancing.

U.S. Pat. No. 6,070,839 (2000) discloses a further design having a pivoting arm and a cable pull-spring construction which permits pure balancing—in the sense of the above-mentioned diagonal parallel carrier arm compensation in the MS 1—but without also contributing balancing moments to an improvement in the tilt safety. In the case of changes in weight, the pivoting point of the cable pull is displaced over a spindle, in a way comparable to the design in the aforementioned DD 221571.

U.S. 5,253,832 (1999) describes a stand having a centrally arranged tension spring for the balancing. This design offers no simple adjustability for changed loads. The tension spring itself has a low inherent weight, so that although it is used for balancing, it is not used for the balance about the vertical mid-axis (tilt safety).

Furthermore, EP 700665 A1 (1995) specifies a stand design which substantially ensures balancing via levers and angled lever arms. In FIGS. 13 and 14 of this published Patent Application, a movement transmission mechanism 157 is presented, which transmits movements of the microscope body about movement axes to a pivoting arm. As a result of this very complicated design with many parts, although a certain amount of balancing is provided, a large number of levers and angled levers is required, since the balancing is ultimately mounted on such levers.

In the MS 1 of the applicant, and in various designs of other known stands, and in the stands specified above, the main support, which accommodates the load directly, is often not fixed directly to the vertical upright column of the stand, but to an additional horizontal arm projecting from this column. Tilt safety is primarily achieved in these designs by an appropriate construction of the stand foot, which must be appropriately large and heavy. The weight compensation, as already specified further above, is effected by a spring diagonally in the parallelogram carrier or by other measures specified above.

An improvement in the tilt safety and a certain compensation for tilt prevention may certainly—as specified above—be made possible by the special arrangement of a switch box or the like.

SUMMARY OF THE INVENTION

By comparison with the known designs, the invention is based on the object of providing a novel type of stand, in particular for surgical microscopes, which is safe against tilting, has the lowest possible volume and has optimum weight compensation. Weight compensation is to be understood, firstly, as compensation for the weight of the load, but secondly also the compensation of any changes in this weight.

This object is achieved, firstly, by a system in which, via a cable pull and at least one deflecting roller, a constant balancing force, for example a weight for the weight compensation, is used, the weight being accommodated either in the vicinity of the upright column, for example on the side opposite the load, concentrically with the upright column or, preferably, within the upright column.

The overall center of gravity of the stand is therefore located relatively low down and can be moved in the direction of the upright column or stand foot, so that the tilting behaviour is already improved for this reason.

By means of the cable pull according to the invention and the at least one deflecting roller, it is additionally possible to fit the balance weight at virtually any desired points or to lead the cable pull over support arms (horizontal arm) or support arm parts of a very wide range of designs, without any noticeable requirement for space and without any noticeable additional weights above the cable pull.

Although a floor stand has already been disclosed (standard and universal) which uses a plastic tape over a deflecting roller in order to connect a balance weight in an upright column with a ring around the upright column, the ring supports an arm that projects horizontally on which the load can be mounted. This design does not permit any load compensation in the case of a pivotable support and, in particular, it does not permit any balancing in the case of a carrier that can be pivoted in a horizontal plane (can be pivoted about the upright column and about a further axis). Since the balance weight or the tapes do not act directly on the pivoting arm, the upright column or the pivot of the support arm on the upright column are subjected to high canting loading (torque of the arm on the upright column). In addition, the known design, in the event of a change in weight at the load, requires a change to the balancing weight by adding or removing weights. If this is not done, the ring has to be fixed to the upright column in order to prevent drift. Automatic balancing is thus not overall possible in the case of this known design.

A preferred embodiment of the invention results from its being considered together with the U.S. patent application 10/010,103 (now U.S. Pat. Nos. 6,708,936, 10/008,285 (now U.S. Pat. No. 6,637,274), and 10/007,168 (now U.S. Pat. No. 6,691,960 filed on the same date and referenced above, which count as lying within the scope of the disclosure of this application and which, for the purpose of subsequent combination of at least two of these applications for foreign applications, can be considered together. The details of a counterbalancing transmission, a cable safeguard and a weight-change measurement, specified in the aforementioned patent application, can be taken directly from these applications for the purpose of combination with the teaching of the present application.

However, the invention is not restricted to the embodiment of a corresponding counterbalancing transmission. Rather, those skilled in the art, given knowledge of the teaching of this invention, will deduce a large number of different designs which, overall, take advantage of the balancing principle of the present invention.

In developments of the invention, it proves to be expedient if the cable pull is rotationally decoupled, that is to say if pivoting the support arm in a horizontal plane does not load the cable in torsion, or any torsion loading which may arise is dissipated at the rotation decoupling points. As an alternative or in addition, use can also be made of cables whose design is tolerant to torsion loadings. Such cables are, in particular, for example left-right braided cables, or combinations of left and right-braided cables.

A special development of the invention provides for the balance weight to be suspended via a block and tackle roller, so that there is multiplication of the force, and the weight of the balanced weight can be selected to be particularly high, which leads to improved stability of the stand, because of the center of gravity being located particularly low down.

Conversely, the scope of the invention includes a special embodiment in which, with the aid of an inverted block and tackle system, the balance weight can be dimensioned to be only half as large, by the step-up ratio in the case of the balance weight leading to an increased distance but to an increased resultant force for the balancing.

Apart from a block and tackle, according to the invention any desired transmission variants via a roller mechanism are possible, in which the cable pull is interrupted and, at the interruption point, acts on one side on a roller with a larger diameter and, on the other side, the other end of the other portion of the cable pull acts on a smaller roller rigidly connected to this roller, so that the force of the balance weight is stepped up or stepped down. Instead of rollers, comparable lever mechanisms can also be used.

Another refinement of the invention provides a type of balance beam as support arm for the load which, at its end facing away from the load, has a guide along which the point of action of a cable pull (sliding pad) can be displaced. At its other end, the cable pull is connected to a balance weight, which is fitted so as to float freely vertically in the area of the upright column.

A preferred and simple construction provides for a roller which is displaceably mounted on a balance arm and acts on a bracket which cannot be displaced, on which the cable pull acts. By means of this construction, when the support arm is pivoted, the proportional change at the action point of the roller on the bracket is automatically adapted, so that the opposing moments have the same proportion to each other in every angular position.

If an additional horizontal arm is used, such as in the case of MS 1, in this way a universal stand which can be pivoted via two vertical axes and has exceptional balancing and improved tilt safety is provided. However, if the tilt safety is left in accordance with the prior art, then the invention permits a higher loading on the support arm and/or on the horizontal arm.

BRIEF DESCRIPTION OF THE DRAWINGS

The invention, variants and developments thereof will be explained in more detail by using exemplary sketches, in which.

The figures are described in an overlapping fashion, identical reference symbols signifying identical components. Reference symbols with identical numbers but different indices signify slightly different components with identical tasks and/or similar effects.

DETAILED DESCRIPTION OF THE INVENTION

Figure 1:
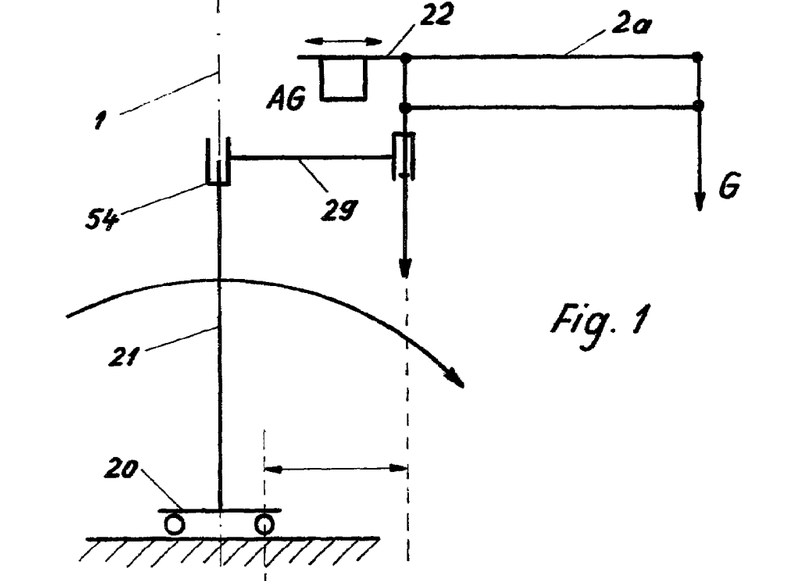
FIG. 1 shows in symbolic form a theoretical design having at least two vertical axes and a balance weight on a balance principle which, for reasons of too low a tilt safety, has been rejected by the present invention.

FIG. 1 shows an example of a conceivable balancing measure on the balance principle, which would be carried out about the vertical axis 1 of the point of attachment of the support arm 2a. Such a measure could initially not improve the tilt safety of the stand, however, since, because of the horizontal support arm 29, the additional weights AG which might be fitted are initially still on the same side of the vertical upright column 21, on which the load G also acts. (Tilting moment according to the arrow over the effective distance k). Only if the balance arm 22 were to be made appropriately long and braked at the pivoting point, in which case it would also project beyond the axis of the upright column 21, could the tilt safety also be improved at the same time with such a balancing system. Here, however, the volume of the overall design would disadvantageously be increased considerably. When the brake were released, tilting might occur. Apart from this, in the case of the conventional stands, the main support arms can be pivoted not only vertically about their mounting points but also laterally, as a result of which positions (the support arm 2a pivoted through about 90° from the plane of the figure) could arise in which, even with lengthened balancing compensation systems, the entire load comes to lie on one side of the upright column 21, and therefore the risk of tilting would become high again. This would have to be compensated for—as attempted in practice—by a sufficiently large or heavy stand foot 20.

Figure 2:
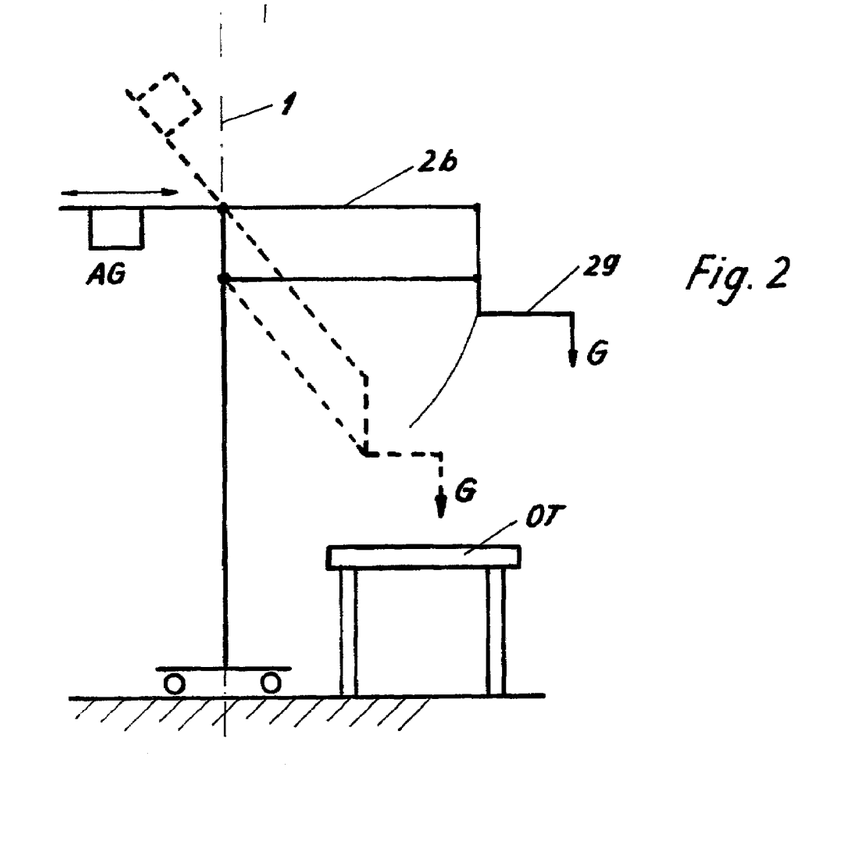
FIG. 2 shows a variant of the design according to FIG. 1, in which the parallelogram carrier is fixed directly to the vertical upright column; this variant has likewise been rejected by the invention, since it restricts the free working space to too great an extent.

FIG. 2 reveals a variant of the design according to FIG. 1, in which the point of attachment of the parallelogram carrier 2b has been displaced to the vertical column 21 of the stand. Although the tilt behavior has been improved by this method, since the balance weight AG is located on the left-hand side of the vertical axis 1, as the sketch indicates, in this design the result is only inadequate clear space for the user within the circle. The parallelogram carrier 2b penetrates into the space which remains clear in the design according to FIG. 1. This leads to the user being hampered, for example when working on an operating table OT, as indicated symbolically.

Figure 2A:
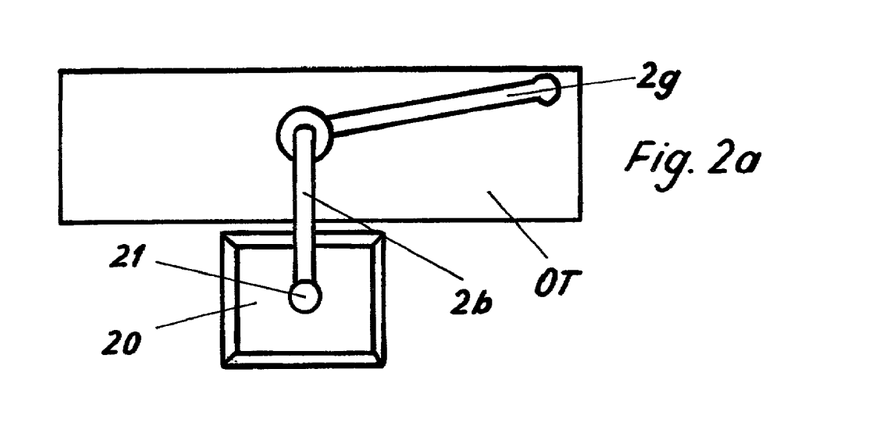
FIG. 2a shows a plan view of a design according to FIG. 1 or 2 in the working position.

FIG. 2a shows the plan view of the working position of the microscope according to FIG. 1 or 2.

Figure 3:
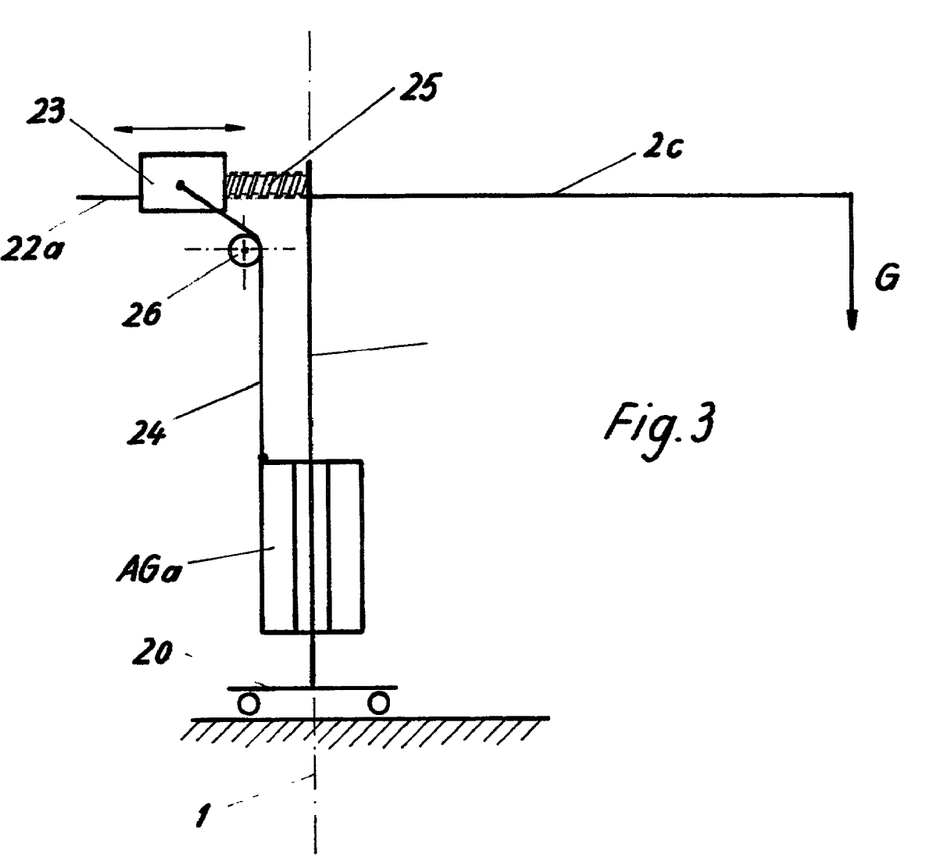
FIGS. 3 and 3a show a design according to the invention on the balance principle.

By contrast, the basic design of a stand according to the invention and according to FIG. 3 is different, in as much as the balance weight is designed in the form of a balance load AGa that can be moved freely vertically and whose point of action is mounted on the balance-like balance arm 22a, which constitutes an extension of the support arm 2c. A sliding pad 23, to which a cable pull 24 is fixed, can be displaced along the balance arm by means of a spindle 25. If the sliding pad 23 is shifted further to the left, the effect (moment) of the balance weight AGa is increased, and the load G can be dimensioned to be greater. The cable pull 24 could in theory form a direct connection between the sliding pad 23 and the balance weight AGa. However, in the case of such a direct connection, when the support arm 2c was pivoted, a cosine error in the effective balance weight would be produced as a result of the oblique position of the cable pull 24.

In the improved embodiment illustrated, however, the cable pull acts on a deflecting roller 26, whose point of rotation is rigidly fixed in relation to the stand column 21. This has the effect that the cable of the cable pull 24 in the region of the balance weight AGa and above does not leave its position parallel to the upright column 21. In its region above the deflecting roller 26, the cable of the cable pull 24 follows the sliding pad 23, however, so that there an oblique position of the cable in relation to the upright column 21 is possible.

Figure 3A:
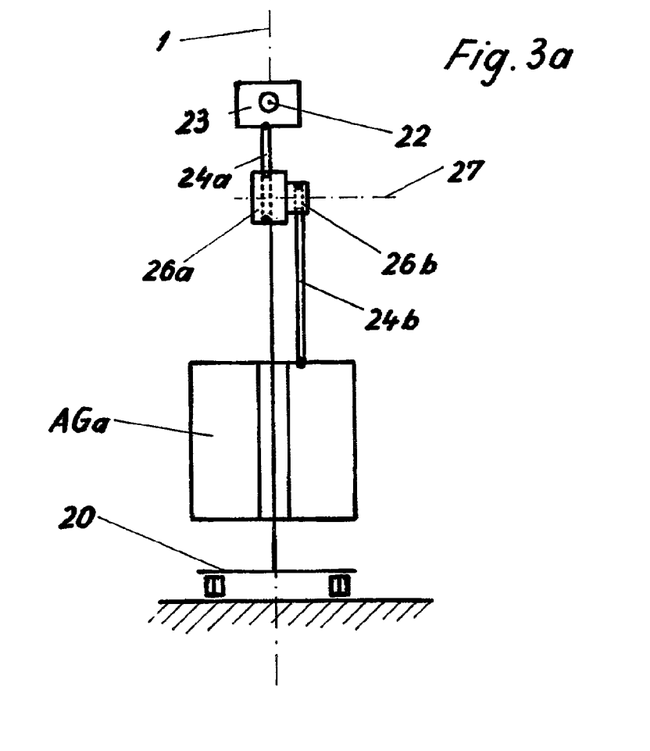

FIG. 3a shows a variant of this deflecting roller 26, which is used at the same time as a step-up transmission; the cable pull 24 is divided into two in this variant, the upper part 24a being connected at one end to a roller 26a and being fixed at the other end to the sliding pad 23. The sliding pad 23 slides on the balance arm 22, which is held by the upright column 21. A smaller deflecting roller 26b is rigidly connected to the larger 26a. The lower cable pull 24b is fixed or wound onto the smaller deflecting roller 26b and, at the other end, is connected to the balance weight AGa. Displacing the sliding pad 23 along the balance arm 22 therefore leads to rotation of the deflecting roller 26a and to a rotationally simultaneous rotation of the deflecting roller 26b about the axis of rotation 27.

Since the radial distance of the cable pull 24b from the axis of rotation 27 of the deflecting roller 26b is lower than the radial distance of the cable pull 24a from the axis of rotation 27 of the deflecting roller 26a, this leads to a step-down ratio, that is to say the balance weight AGa can be significantly larger than it would have to be if the cable pull 24a were connected directly to the cable pull 24b. For cases in which the balance weight is to be smaller, the two rollers 26a and 26b are interchanged, which results in a step-up ratio, in which a lower balance weight achieves a greater balancing effect than in the case previously described.

In FIGS. 3 and 3a, the balance weight AGa is symbolically arranged annularly around the upright column 21. Within the context of the invention, however, solutions are in particular provided in which the balance weight is arranged inside the upright column 21 or else only on the side of the upright column 21 which is opposite the load G around the axis 1.

Figure 4:
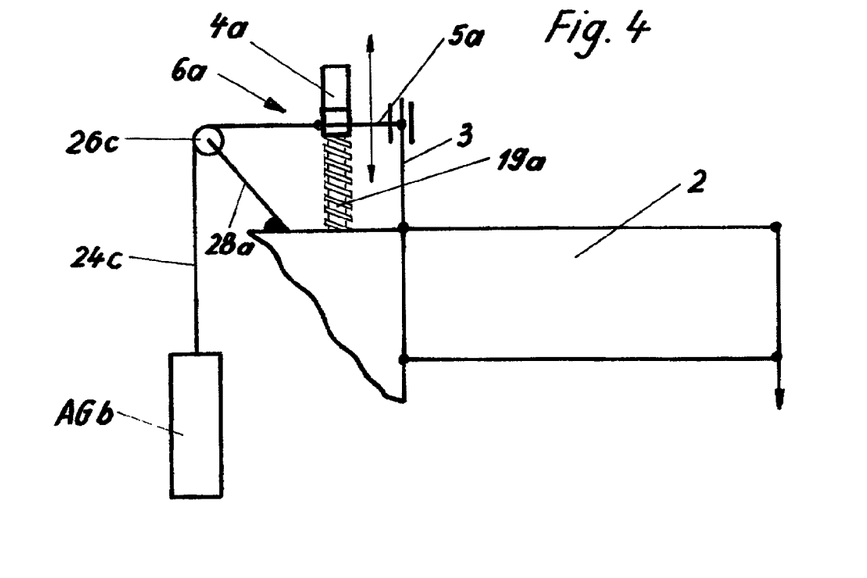
FIGS. 4 and 5 show variants of a design according to the invention with a counterbalancing transmission but without cosine compensation.

FIG. 4 reveals a design without a balance arm 22. In the case of this design, an arm 3 which is rigidly connected to the support arm 2 takes over the balancing function—as in the case of U.S. patent application Ser. No. 10/008,285 (now U.S. Pat. No. 6,637,274). Provided parallel to said arm 3 is an arm 4a, which has a spindle 19a. Articulated on the two arms 3 and 4a is a connecting arm 5a, which can be adjusted in terms of its height by means of the spindle 19a. Connected to the connecting arm 5a is a cable pull 24c, which is led around a deflecting roller 26c and bears the balance weight AGb at its other end. The roller 26c can, if required, likewise be of two-part design, corresponding to the illustration in FIG. 3a, and can have a step-down or step-up function.

Figure 5:
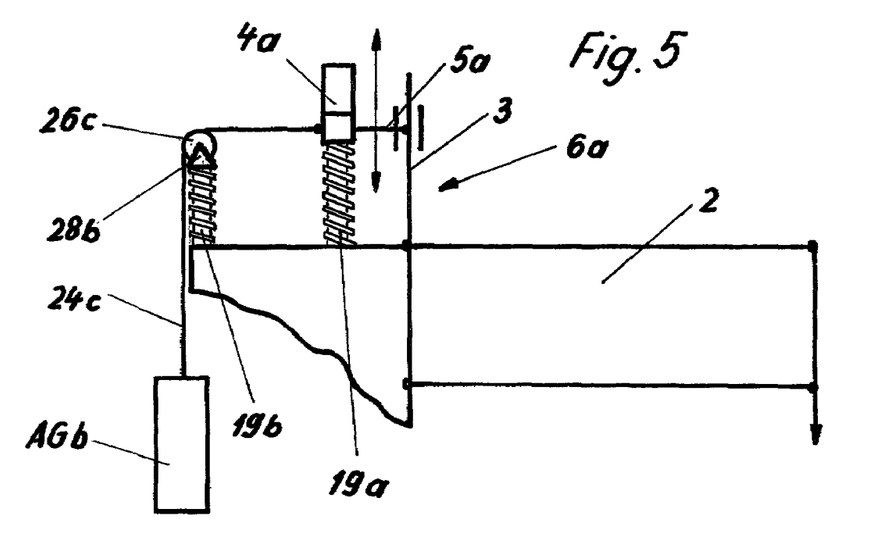

The design of FIG. 5 is to be understood as a variant of the design of FIG. 4, in which, firstly, the parallelogram 6a acting as a counterbalancing transmission is provided, but secondly, instead of a simple support 28 according to FIG. 4 for the deflecting roller 26c, a spindle-controlled support 28b is provided, which makes it possible to change the position of the deflecting roller 26c as well, in parallel with the displacement of the connecting arm 5a. Although this means greater mechanical effort and more expenditure on components, the balancing behaviour of the overall arrangement is improved.

Figure 6:
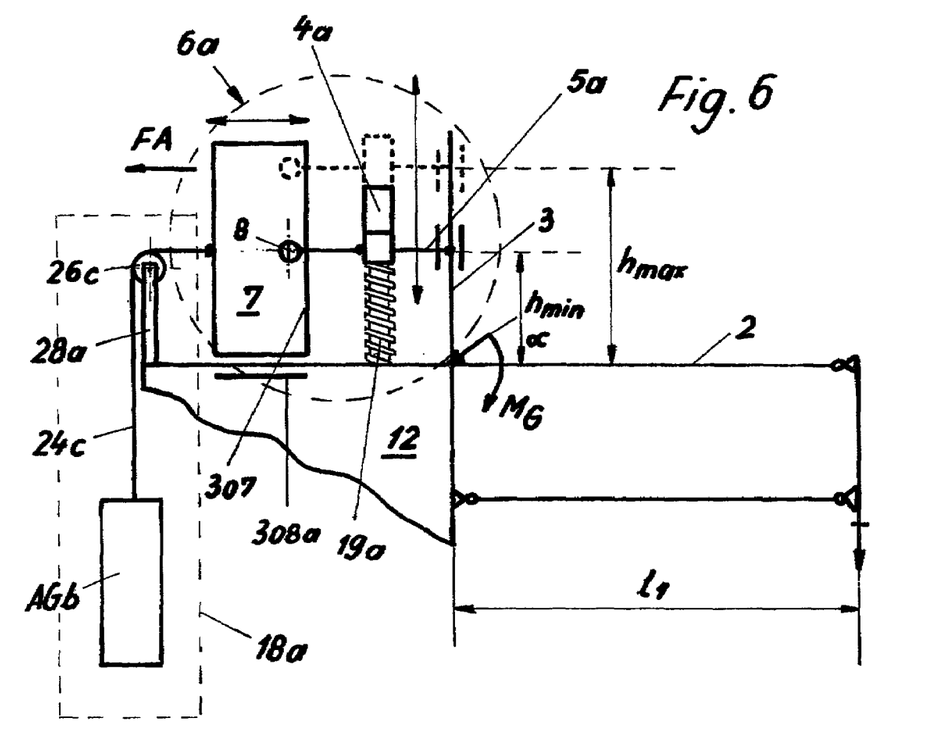
FIG. 6 shows a variant of a design according to the invention with cosine compensation.

FIG. 6 corresponds to the design according to the aforementioned U.S. patent application Ser. No. 10/008,285 (now U.S. Pat. No. 6,637,274). As distinct from the design of the load-equalizing unit 18 in the aforementioned application, the corresponding unit 18a in the present case is constructed from the cable pull 24c, the deflecting roller 26c and the balance weight AGb. In the event of displacement of the spindle 19a, there is a displacement of the height of the connecting arm 5a on the cheek of a carriage 7, which can be displaced laterally relative to the basic body 12. Via the cable pull 24c, which is connected to the carriage 7, the constant balancing force FA is applied to the carriage and therefore to the connecting arm 5a, which is associated with the corresponding step-up ratio for changes in weight at the load G merely as a result of its distance from the basic body 12.

As already described in U.S. patent application Ser. No. 10/008,285 (now U.S. Pat. No. 6,637,274), G indicates the load or the surgical microscope which is held at the distal end of a pivotable parallelogram carrier 2. The upper arm of the parallelogram carrier 2 is rigidly connected to an arm 3, which is connected by a further parallel arm 4 and a connecting arm 5 to a further parallelogram 6a.

This parallelogram 6a forms the counterbalancing transmission, in which the connecting arm 5a can be adjusted vertically in terms of its parallel position, as a result of which the geometry of the parallelogram 6a can be changed by means of a spindle 19a. Pivoting the parallelogram carrier 2 upwards or downwards leads to the parallelogram 6a being pivoted to the left or to the right.

The dashed line $h_{max}$ indicates the outermost position of the connecting arm 5a, at which there is the greatest leverarm step-up ratio, that is to say at which G can assume the greatest load. In addition, FIG. 4 of U.S. Patent Application Serial No. 10/008,285 (now U.S. Pat. No. 6,637,274) reveals how, during the pivoting operation of the parallelogram carrier 2, the geometry of the parallelogram 6a changes, which results in an automatic compensation effect (cosine compensation) in the balancing forces.

This is in accordance with the formula M(G)=M(F) or 11×G−h1×F or 12×G−h2×F, where M(G) is the moment of the load and M(F) is the moment of the counter balancing force.

$$l2 = l1 \times \cos\alpha$$
$$h2 = h1 \times \cos\alpha \frac{l2}{h2} = \frac{l1 \cdot \cos\alpha}{h1 \cdot \cos\alpha} = \frac{l1}{h1}$$

In the event of a change in the weight at G, according to the invention, therefore, it is merely necessary to shift the connecting arm 5a in parallel along the arm 3 in order to change $h_{min/max}$ accordingly, in order that the compensation for the change in weight is achieved with a constant balancing force FA.

In FIGS. 4 to 6, the weight AGb is illustrated as being suspended freely. In practice, this will naturally be accommodated in a cage, on a guide rod or in the upright column of the stand, as indicated, for example, in FIGS. 7 and 8.

Figure 7:
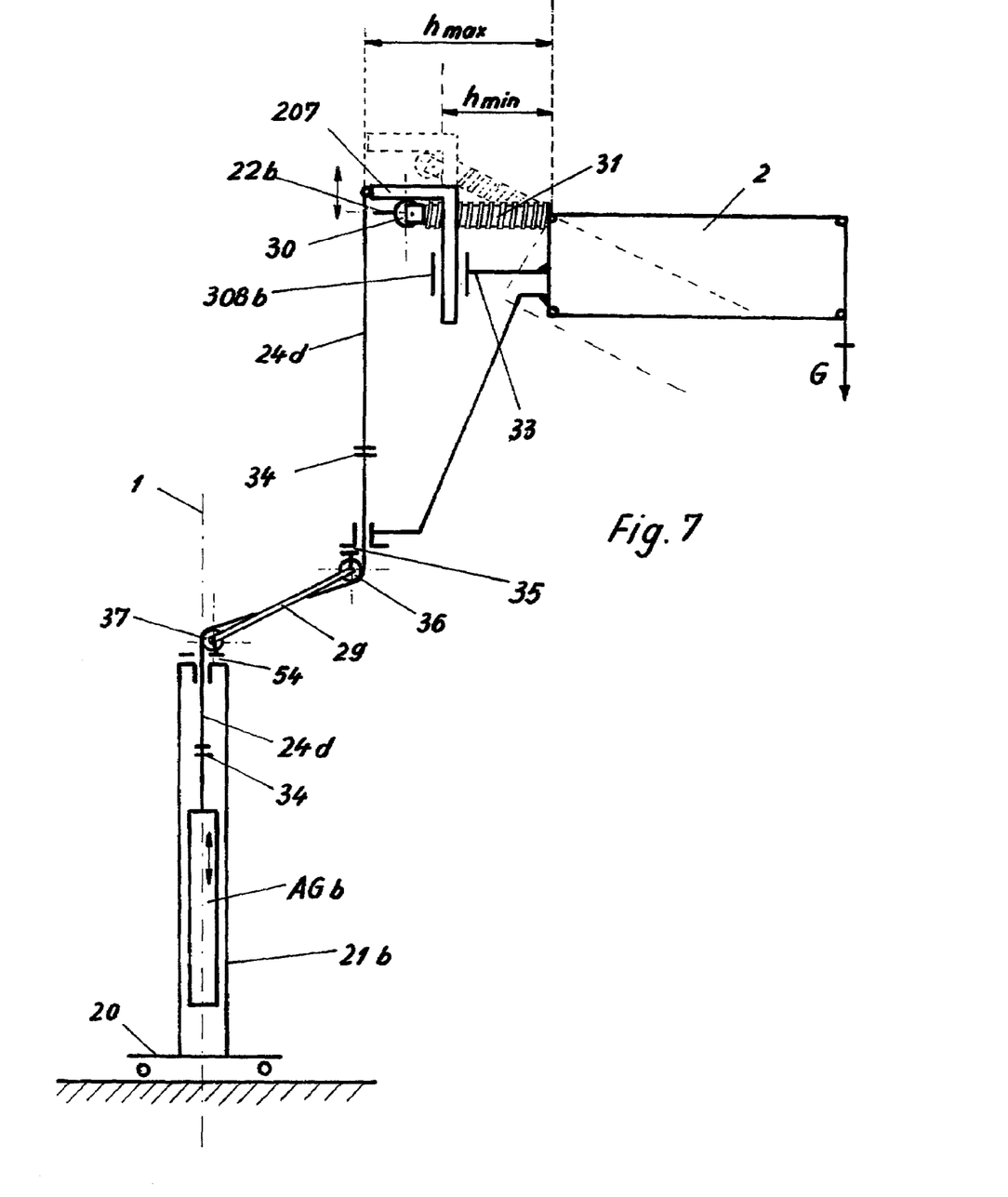
FIG. 7 shows a design with a modified counterbalancing transmission and cable pull via a horizontal arm with cosine compensation.

The design according to FIG. 7 differs from that of FIGS. 3 to 6 principally by an additional horizontal arm 29, which carries the support arm 2 such that it can pivot about a vertical and about a horizontal axis. Provided between the horizontal arm 29 and the support arm 2 is a different form of the counterbalancing transmission than that described hitherto: a supporting roller 30 can be displaced by means of a spindle along a balance arm 22b. In this case, it is unimportant whether the roller 30 is seated on a nut or whether it is mounted on a sliding pad which can be displaced longitudinally on a rod (lengthening the upper arm of the support arm 2) by means of a parallel threaded spindle.

A bracket 207 rests on the roller 30 and, on one side, is guided in a parallel guide 33 belonging to the counterbalancing transmission and fixed to the housing. On the other side, it is connected to the cable of the cable pull 24d. If the roller 30 is displaced longitudinally by the spindle 31, then this leads to a different point of action of the balance weight on the balance arm 22b via the cable pull 24d. At the point 34, the cable pull 24 is rotationally decoupled, in order that the support arm 2 can pivot in a horizontal plane about a bearing 35.

Provided along the horizontal arm 29 are two further deflecting rollers 36 and 37, which guide the cable pull 24d into the interior of the support column 21b. Located in the interior of this support column 21b is the balance weight AGb, which is preferably once more rotationally decoupled via a rotary coupling 34. The balance weight AGb is preferably designed in at least two parts, for reasons of transport and for easier mounting on site.

As can be seen, this design needs only a minimum amount of space. On the other hand, the relatively heavy balance weight AGb is distributed symmetrically about the vertical axis 1 of the support column 21b, and advantageously effects a lowering of the overall center of gravity in the direction of the stand foot 20.

The design of FIG. 7 also falls under the protective cover of claims 1–5 of U.S. Patent Application Serial No. 10/008, 285 (now U.S. Pat. No. 6.637.274). Various reference symbols in FIG. 7 have the following correspondences: the balance arm 22b corresponds approximately to the arm 3 from FIG. 6.

The spindle 31 carries out approximately the same function as 19a from FIG. 6. The bracket 207 has a comparable function to that of the carriage 7 or its cheek 307 from FIG. 6, and the roller 30 is approximately functionally equal to the roller 8 from FIG. 6. The effective lengths $h_{max}$–$h_{min}$ on the balance arm 22b correspond to the lengths $h_{max}$–$h_{min}$ on the arm 3 from FIG. 6. The cosine correction is ensured in both designs by the guide 308a (FIG. 6), and 308b (FIG. 7).

Figure 8:
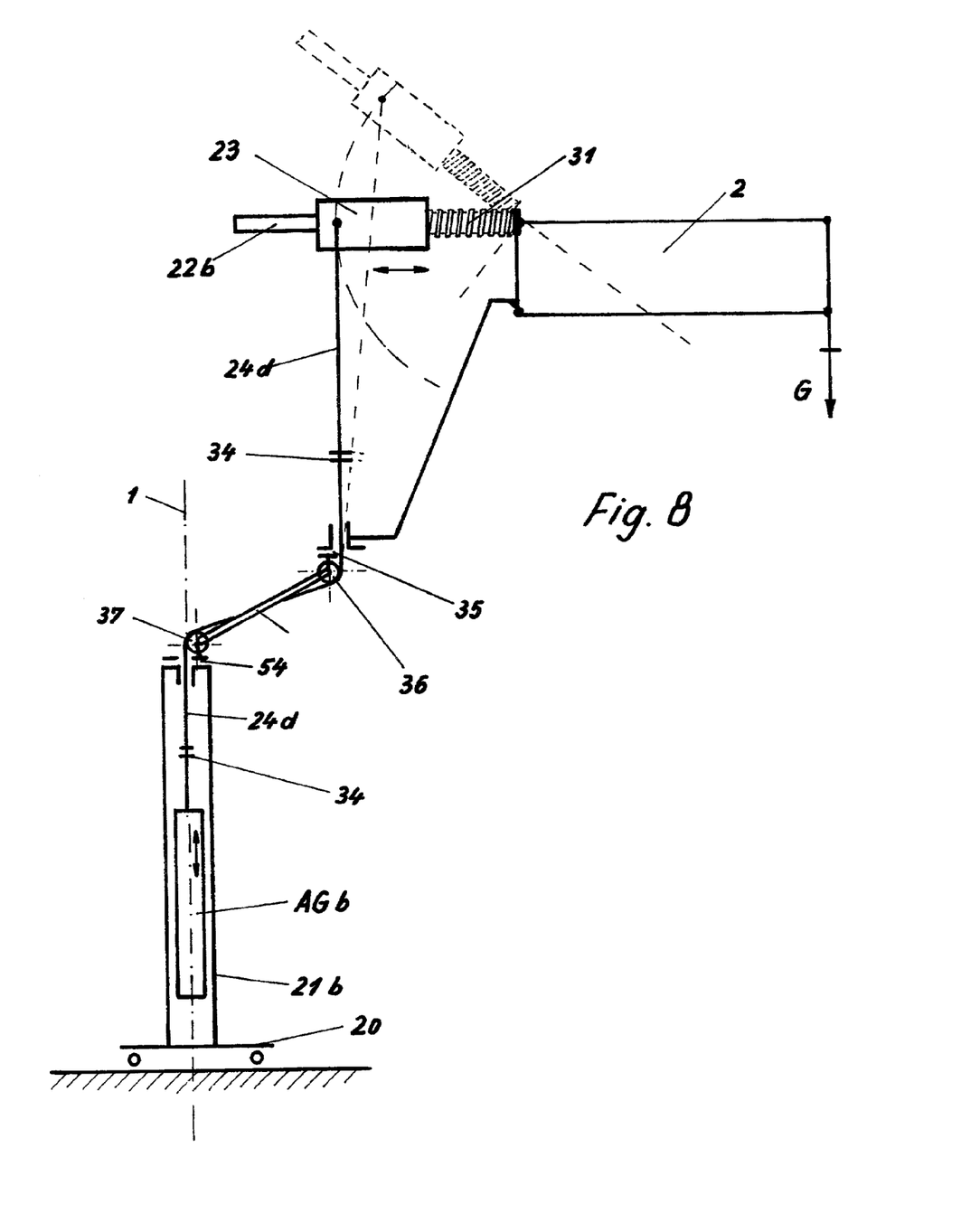
FIG. 8 shows a variant of the design according to FIG. 7 without cosine compensation.

The design of FIG. 8 is a simplified design according to FIG. 7 and dispenses with the roller 30 and with the bracket 207. Instead, the fixing point of the cable pull 24d is merely defined on a sliding pad 23, which can be displaced along the balance arm 22b via the spindle 31. If required, one of the rollers 36, 37 can be designed as a geared roller corresponding to the design according to FIG. 3a, in order to effect a step up or a step down on the cable pull 24d.

Since, between the $h_{min}$ and $h_{max}$ settings, a different effect of the direction of action of the cable pull on the sliding pad 23 occurs, there is no adequate cosine compensation. Under certain circumstances, this leads to a variable compensation action occurring as a result of the balance weight AGb, depending on the pivoting position of the support arm 2, so that the user may notice an imbalance, for which reason this design is not preferred. On the other hand, however, such a design according to the invention, as compared with a design with diagonal spring support, can be produced with a greater loading with the same tilt stability.

Figure 9:
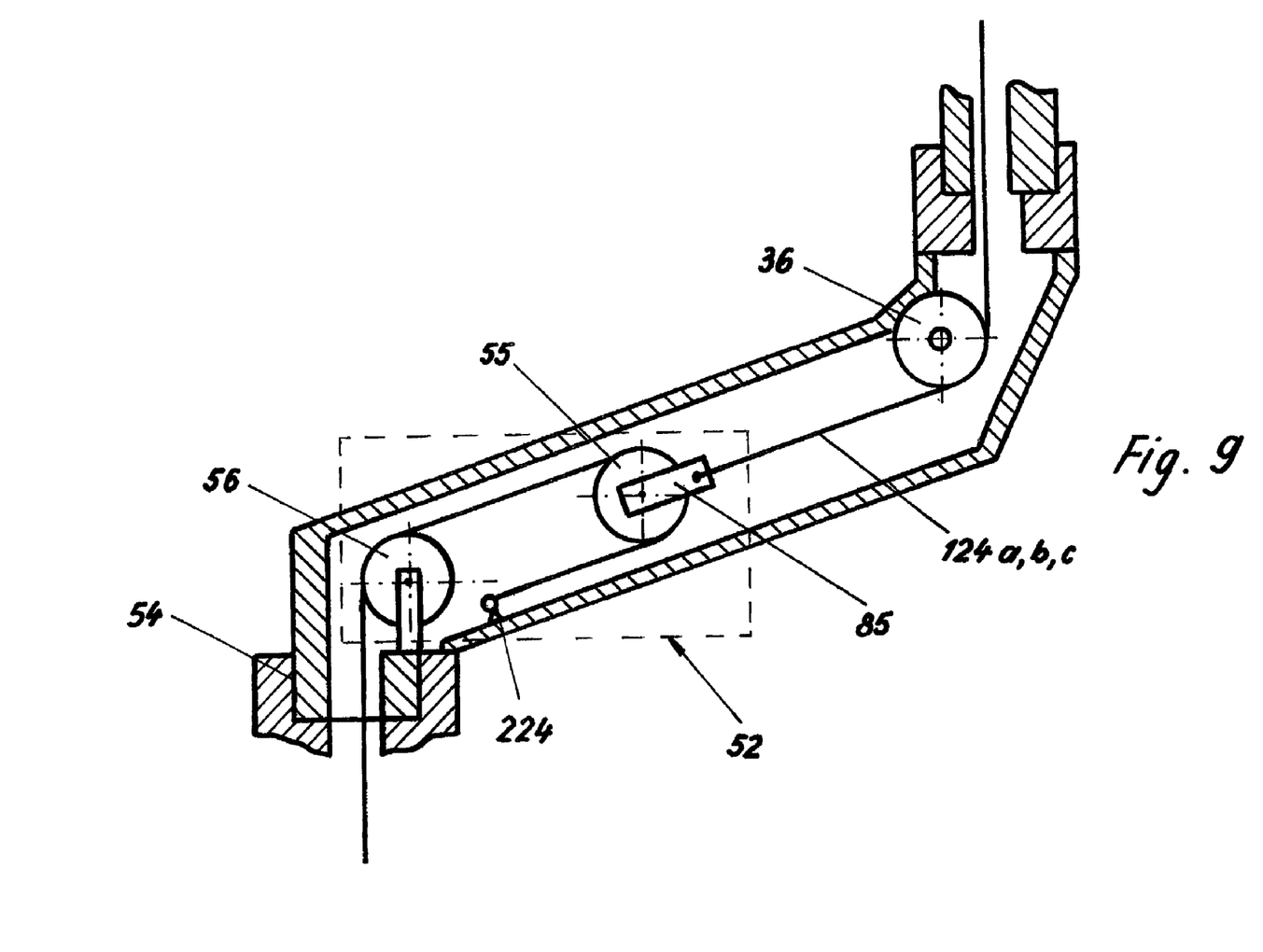
FIG. 9 shows a symbolic illustration of the block and tackle within the cable pull.

In addition, such a design can be produced particularly cost-effectively. FIG. 9 reveals a cable pull designed in accordance with the invention, having a simple block and tackle. The latter comprises a roller 55, which is positioned such that it can move between the rollers 36 and 37. The cable pulls 24a–c wrap around the roller 55 and are fixed to the housing at 224. In this design, therefore, the result is a step-up ratio of 2:1. Within the context of the invention, other step-up ratios are also possible. Those skilled in the art are aware of comparable block and tackle systems for hoists.

Figure 10:
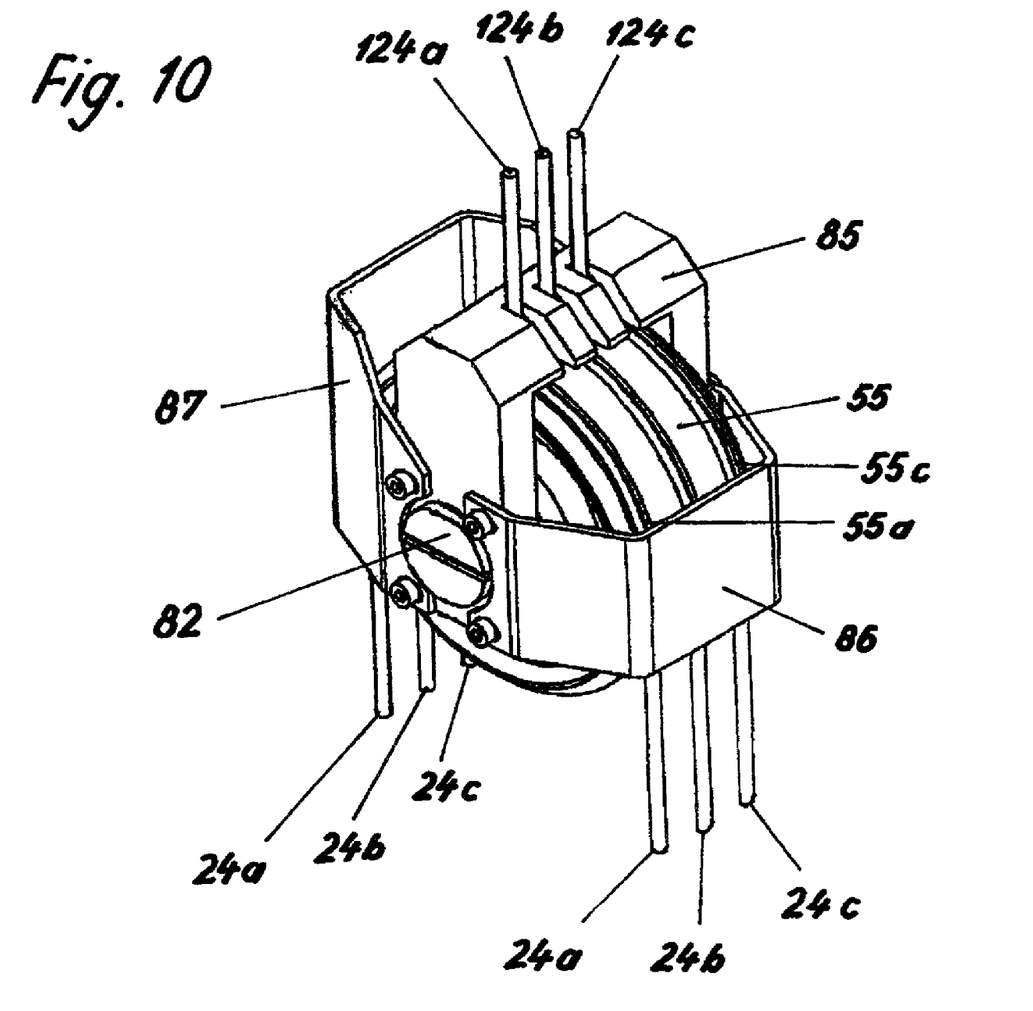
FIG. 10 shows the upper part of the block and tackle in an oblique view.

FIG. 10 reveals details of the roller 55 of the block and tackle 52, which has three parallel guide grooves 55a, 55b and 55c, in order to accommodate therein the three cables from the cable pull 24a, 24b and 24c. The roller 55 bears a roller frame 85 and the latter is in turn connected to the holding cable pulls 124a, 124b and 124c, which transmit the tensile force, for example to the bracket 207 (FIG. 7) or to the sliding pad 23 (FIG. 8).

Figure 11:
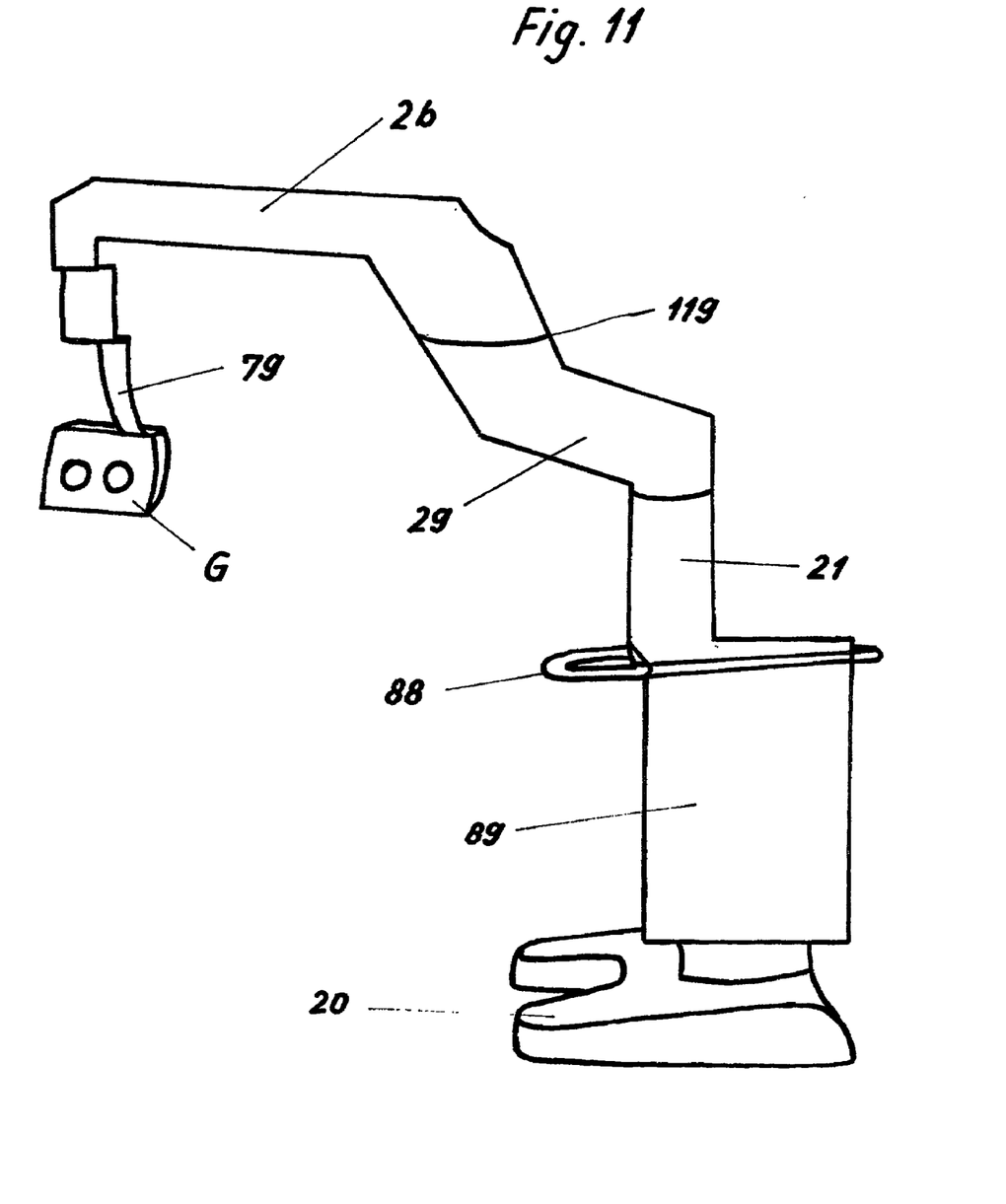
FIG. 11 shows a stand design with a surgical microscope as load.

FIG. 11 reveals a stand construction designed in accordance with the invention, having a microscope as the load G on a pivoting carrier 79, which is held by a parallelogram carrier 2b of integral design. The carrier 2b is pivotably mounted at a bearing point 119 on a horizontal arm 29, which is mounted on the upright column 21. A bow grip 88 serves as a transport aid, and an equipment box 89, in addition to accommodating control systems, power supply, illumination and so on, also serves as an additional improvement to the tilt stability, corresponding to the MS 1 design.

In the present invention, reference is always made to a balance weight. Given knowledge of the invention, those skilled in the art will understand that, instead of the balance weight, other balancing force-producing measures; such as tension springs or the like, can also be provided without leaving the essence of the invention. In this case, however, care must be taken that these tension springs or the like produce a constant balancing force. In this point, the invention also differs significantly from the known prior art US 5253832. The novel inventive design of the applicant according to U.S. patent application Ser. No. 10/008,285 (now U.S. Pat. No. 6.637,274) provides an example of such a force-compensated solution with a spring.

Carriers in the sense of the patent claims are to be understood both as individual support arms and parallelogram carriers or similar constructions.

PARTS LIST

1—Vertical axis of the vertical support
2—Support arm and/or parallelogram carrier
3—Arm
4a—Arm
5a—Connecting arm
6a—Parallelogram carrier and/or counterbalancing transmission
7—Transfer element, preferably carriage or slide
8—Roller
12—Supporting component and/or basic body
18a—Spring unit and/or load-equalizing unit
19a, b—Spindle
20—Stand foot
21b—Support column
22b—Balance arm
23—Sliding pad
24a, b, c, d—Cable pull
25—Spindle
26a, b, c—Deflecting roller
27—Axis of rotation
28a, b—Support
29—Horizontal arm, could also be inclined
30—Roller
31—Spindle
33—Parallel guide
34—Rotary coupling
35—Bearing
36—Roller
37—Roller
54—Bearing point
55a, c—Block and tackle rollers
56—Block and tackle rollers
79—Pivoting carrier
82—Hub
85—Roller frame 86—Safety frame
87—Fastening frame
88—Bow grip
89—Equipment box
119—Pivot bearing
124a, b, c—Holding cable pull
207—Transfer element for example bracket
224—Pivoting point for cable pull 24
307—Cheek of the carriage 7
308b—Guide for carriage 7
AG,a, b—Balance weight
G—Load and/or weight of the microscope
FA—Constant balancing force
OT—Operating table
MG—Moment produced by G about the pivoting point of the upper support arm of the parallelogram carrier 2b.

What is claimed is:

1. A stand for supporting a surgical microscope, said stand comprising:
    an upright column;
    a support arm connected to said upright column for carrying said surgical microscope, said support arm being pivotable in a vertical plane;
    a cable pull operatively connected to said support arm to act at a location spaced from a pivot axis of said support arm; and
    a device for applying a constant balancing force to said support arm through said cable pull to compensate for loading associated with said surgical microscope; and
    at least one deflecting roller mounted on said stand for redirecting said cable pull in a direction parallel to said upright column for connection to said device, wherein said at least one deflecting roller redirects said cable pull to extend at least closely along a vertical axis of said upright column.

2. The stand according to claim 1, further comprising a generally horizontal arm linking said pivotable support arm to said upright column.

3. The stand according to claim 2, wherein said at least one deflecting roller redirects said cable pull to extend within said upright column.

4. The stand according to claim 1, further comprising a counterbalancing transmission having a transmission element for connecting said cable pull to said support arm, wherein said cable pull is fixed to said transmission element.

5. The stand according to claim 1, further comprising a counterbalancing transmission having a movable transfer element coupled to a transmission element for connecting said cable pull to said support arm, wherein said cable pull is fixed to said transfer element.

6. The stand according to claim 5, further comprising a basic body to which said support arm is pivotably mounted, wherein said transfer element is a carriage mounted on said basic body for displacement relative to said basic body.

7. The stand according to claim 5, further comprising a basic body to which said support arm is pivotably mounted, wherein said transfer element is a bracket mounted on said basic body for displacement relative to said basic body.

8. The stand according to claim 5, wherein said transmission element is adjustable in its position with respect to said transfer element.

9. The stand according to claim 8, wherein said transmission element is adjustable in its position with respect to said transfer element by means of a spindle.

10. The stand according to claim 1, wherein said device for applying a constant balancing, force comprises a balance weight.

11. The stand according to claim 10, further comprising a block and tackle for suspending said balance weight.

12. The stand according to claim 11, wherein said balance weight is arranged such that it can move freely vertically within said upright column.

13. The stand according to claim 11, wherein said balance weight is arranged such that it can move freely vertically alongside said upright column in close proximity to said upright column.

14. The stand according to claim 13, further comprising a low-friction bearing for guiding said balance weight along said upright column.

15. The stand according to claim 9, further comprising means for automatically driving said spindle to cause adjustment.

16. The stand according to claim 15, wherein said means for automatically driving said spindle comprises an electric motor.

17. The stand according to claim 15, wherein said means for automatically driving said spindle comprises an electromagnetic drive.

18. The stand according to claim 15, wherein said means for automatically driving said spindle comprises a hydraulically actuated drive.

19. The stand according to claim 15, wherein said means for automatically driving said spindle comprises a pneumatically actuated drive.

20. The stand according to claim 15, wherein said means for automatically driving said spindle includes a brake.

21. Stand according to claim 15, wherein said means for automatically driving said spindle is computer-controlled.

22. The stand according to claim 21, further comprising a measuring sensor associated with said support arm for determining a change in load, wherein output data from said measuring sensor is used for controlling said spindle adjustment.

23. The stand according to claim 1, further comprising an equipment box arranged on said upright column, whereby said equipment box acts as a stabilizing weight for said stand.

24. The stand according to claim 1, further comprising a generally horizontal arm linking said pivotable support arm to said upright column, wherein said horizontal arm can be pivoted in a horizontal plane on said upright column and said horizontal arm mounts said support arm on said stand such that said support arm can be pivoted in a horizontal plane.

25. The stand according to claim 24, wherein said cable pull is interrupted at least once by a rotational decoupling means for preventing torsion in said cable pull.

26. The stand according to claim 24, wherein said cable pull includes a torsion-tolerant cable.

27. The stand according to claim 1, wherein said cable pull is interrupted by a step-up or step-down transmission.

28. The stand according to claim 27, wherein said step-up or step-down transmission comprises at least two deflecting rollers firmly connected to each other so as to rotate with each other, said at least two deflecting rollers having different diameters.

29. The stand according to claim 1, further comprising a balance arm rigidly connected to said support arm and a sliding pad displaceably arranged on said balance arm, wherein said cable pull is fixed to said sliding pad.

30. The stand according to claim 29, wherein said sliding pad can be adjusted by means of a spindle in terms of its position along said balance arm.

31. The stand according to claim 2, wherein the position of said at least one deflecting roller is adjustable by means of a spindle.

32. The stand according to claim 5, further comprising a basic body to which said support arm is pivotably mounted, wherein said transfer element is a carriage between said counterbalancing transmission and said at least one deflecting roller, said carriage being mounted such that it can be displaced with respect to said basic body and serving to transmit force between said cable pull and said counterbalancing transmission.

33. The stand according to claim 10, wherein said balance weight comprises at least two partial weights.

34. The stand according to claim 1, wherein said cable pull comprises two parallel cables.

35. The stand according to claim 34, wherein said two parallel cables have opposite winding directions.

* * * * *